US010123697B2

(12) United States Patent
Rossi

(10) Patent No.: US 10,123,697 B2
(45) Date of Patent: Nov. 13, 2018

(54) APPARATUS AND METHOD FOR AUTOMATIC ALIGNMENT IN AN OPTICAL SYSTEM AND APPLICATIONS

(71) Applicant: UNIVERSITY OF ROCHESTER, Rochester, NY (US)

(72) Inventor: Ethan A. Rossi, Rochester, NY (US)

(73) Assignee: University of Rochester, Rochester, NY (US)

( * ) Notice: Subject to any disclaimer, the term of this patent is extended or adjusted under 35 U.S.C. 154(b) by 112 days.

(21) Appl. No.: 14/482,195

(22) Filed: Sep. 10, 2014

(65) Prior Publication Data

US 2015/0070655 A1 Mar. 12, 2015

Related U.S. Application Data

(60) Provisional application No. 61/875,808, filed on Sep. 10, 2013.

(51) Int. Cl.
*A61B 3/12* (2006.01)
*G02B 21/00* (2006.01)
(Continued)

(52) U.S. Cl.
CPC .............. *A61B 3/12* (2013.01); *A61B 3/0075* (2013.01); *A61B 3/1015* (2013.01);
(Continued)

(58) Field of Classification Search
CPC ....... A61B 3/12; A61B 3/1015; A61B 3/1025; A61B 3/0075; G02B 21/006; G02B 21/0076; G02B 21/0064
See application file for complete search history.

(56) References Cited

U.S. PATENT DOCUMENTS 5,162,641 A * 11/1992 Fountain ................. A61F 9/008
250/201.2
6,713,718 B1 * 3/2004 Lu ......................... B23K 26/032
219/121.69

(Continued)

OTHER PUBLICATIONS

Dubra, A. et al. "Reflective afocal broadband adaptive optics scanning ophthalmoscope" Biomedical Optics Express, vol. 2, No. 6, (Jun. 1, 2011), pp. 1757-1768.*

(Continued)

*Primary Examiner* — Cara Rakowski
(74) *Attorney, Agent, or Firm* — Andrew J. Anderson, Esq.; Harter Secrest & Emery LLP

(57) ABSTRACT

Methods and apparatus for automatically aligning a confocal aperture utilize a confocal imaging system and a computer controlled optimization algorithm such as the Nelder-Mead algorithm for imaging an in-vivo eye having chromatic aberration. When using a confocal aperture of 3.4 Airy disks in diameter, images were obtained using retinal radiant exposures of less than 2.44 J/cm$^2$, which is ~22 times below the current ANSI maximum permissible exposure. The embodied method can be used, e.g., to study RPE morphology in AMD and other diseases, providing a powerful tool for understanding disease pathogenesis and progression, and offering a new means to assess the efficacy of treatments designed to restore RPE health.

21 Claims, 6 Drawing Sheets

(51) Int. Cl.
*A61B 3/10* (2006.01)
*A61B 3/00* (2006.01)
(52) U.S. Cl.
CPC .......... *A61B 3/1025* (2013.01); *G02B 21/006* (2013.01); *G02B 21/0064* (2013.01); *G02B 21/0076* (2013.01)

(56) References Cited

U.S. PATENT DOCUMENTS

2011/0092762 A1* 4/2011 Wong .................. C12N 5/0604
600/34
2012/0236120 A1* 9/2012 Kramer .............. G02B 21/0004
348/46

OTHER PUBLICATIONS

Grieve, K. et al. "Multi-wavelength imaging with the adaptive optics scanning laser Ophthalmoscope" Optics Express, vol. 14, No. 25, (Dec. 11, 2006), pp. 12230-12242.*

* cited by examiner

APPARATUS AND METHOD FOR AUTOMATIC ALIGNMENT IN AN OPTICAL SYSTEM AND APPLICATIONS

RELATED APPLICATION DATA

The instant application claims priority to U.S. provisional application Ser. No. 61/875,808 filed Sep. 10, 2013, the subject matter of which is incorporated by reference in its entirety.

STATEMENT OF GOVERNMENT INTEREST

This invention was made with government support under EY021669, EY007125, EY004367, EY014375, and EY021786 awarded by the National Institutes of Health. The U.S. Government has certain rights in the invention.

BACKGROUND

Embodiments and aspects of the invention are generally directed to methods and associated apparatus for automatically aligning an aperture in an optical system and applications thereof. More particular embodiments and aspects are directed to methods and associated apparatus for automatically aligning one or more pin-hole-sized apertures in an optical system having multiple light sources and light detection wavelengths in one or more channels of an optical imaging system, particularly in the presence of at least certain optical aberrations such as, but not limited to, chromatic aberration. Most particularly, embodiments and aspects are directed to methods and associated apparatus for automatic alignment of a confocal aperture in a confocal imaging system such as, but not limited to, a confocal scanning laser microscope or a fluorescence adaptive optics scanning laser ophthalmoscope (FAOSLO), especially for fluorescence imaging in the human eye where the chromatic aberration of the eye under investigation is unknown. These embodiments and aspects offer, for example, a synergistic enhancement enabling high resolution imaging of individual retinal pigment epithelium (RPE) cells in patients with age-related macular degeneration (AMD).

Drusen and atrophy of the retinal pigment epithelium (RPE) are hallmarks of age related macular degeneration (AMD). Histological studies of postmortem eyes have shown that substantial changes occur in RPE cell mosaic morphology in AMD. These changes may precede and/or accompany RPE cell death and the degeneration of overlying photoreceptors. Clinical imaging methods, such as confocal scanning laser ophthalmoscopy (cSLO), are used to examine the fundus fluorescence (FAF) pattern as a means of assessing the health of the RPE in AMD and other retinal diseases. However, currently available commercial FAF imaging systems lack the resolution to identify individual cells, preventing morphometric analysis of the RPE cell mosaic.

Although imaging of the intrinsic autofluorescence (AF) of lipofuscin has become a relatively common method used in the clinic to assess the health and integrity of the RPE, there are several reasons why higher resolution images of the RPE would be desirable to evaluate patients with diseases affecting the RPE. FAF images obtained using commercial instruments have demonstrated utility for observing the overall patterns of RPE fluorescence seen in disease, but these images are often difficult to interpret. Sophisticated qualitative classification schemes have been proposed but are difficult to implement without trained readers and are limited in their utility. The total absence of an FAF signal is often interpreted as complete RPE atrophy and FAF images can be useful for assessing the extent of RPE loss in geographic atrophy (GA) and its progression rate. However, spectral domain optical coherence tomography (SD-OCT) has been shown to be more precise for measuring lesion size in GA. This is due in part to the variability in fluorescence seen at the borders of GA lesions and by screening of fluorescence due to macular pigment. For these reasons and since the fluorescence signal obtained is not a radiometric measurement (i.e., the images display relative, not absolute AF), the interpretation of hyper-AF and hypo-AF patterns seen in diseased eyes is difficult. These patterns presumably relate to changes in the health and integrity of the RPE cell mosaic, but cellular resolution is needed to understand how RPE cell mosaic morphology relates to the patterns seen in FAF images. Histological studies have shown that RPE mosaic morphology is drastically altered in AMD, but these studies of post mortem eyes are limited in that they only reveal a single time point and cannot compare changes in RPE morphology to other measures, such as cSLO FAF imaging, SD-OCT, or AO reflectance imaging of the photoreceptor cell mosaic. In-vivo cellular resolution imaging has the potential to identify early disease changes in the RPE cell mosaic, before the heterogeneous patterns of hyper-AF and hypo-AF seen in conventional FAF imaging arise. Furthermore, cellular imaging could enable earlier detection of retinal disease, improved understanding of disease etiology, more rapid monitoring of disease progression, and more sensitive metrics for evaluating treatment effects.

By combining fluorescence imaging methods with adaptive optics scanning light ophthalmoscopy (FAOSLO), Gray, Morgan, and colleagues demonstrated that it was possible to image individual RPE cells in-vivo in monkeys. Morgan and colleagues later demonstrated that these methods could be used to achieve single cell resolution of the RPE in the living human eye. Since the RPE is important for maintaining the healthy function of the photoreceptor layer and is implicated in many retinal diseases, such as AMD, the demonstration that these cells were now accessible to optical imaging in the living human eye was a potentially valuable advance. However, the instant inventor's early attempts to image the RPE in patients with AMD using these methods proved difficult; images with greater structural detail than provided by commercial systems were obtained, but individual cells could not be resolved.

This difficulty can be partially attributed to the aging eye, which poses a challenge for imaging even using adaptive optics ophthalmic imaging instruments. Optical challenges that affect image contrast and resolution include increased scatter, lens opacities, and dry eye. Patients with AMD whose central vision is compromised usually have poor fixation, which can increase distortions in scanning system images and make image registration difficult. Moreover, older adults can often have other health problems or mobility issues requiring imaging sessions to be short. All of these factors conspire to make imaging the aging eye more difficult than for younger eyes. Despite having success imaging RPE cells in some healthy young eyes using the fixed dual focus method proposed by Morgan and colleagues, our ability to resolve the RPE mosaic was highly inconsistent. This was due in part to poor compensation of the longitudinal chromatic aberration of the eye. This procedure proved difficult to replicate reliably using manual positioning of the optical elements, such as lenses, light sources, and confocal aperture(s). This is supported by early experiments that suggested that a fixed defocus offset to compensate for chromatic aberration did not appear to work consistently for all observers. This inconsistency was due to a combination of optical alignment and true differences in longitudinal chromatic aberration between participants.

The current standard method for adjusting the focal plane of an AOSLO is to use the deformable mirror to change the focus. This works well when one light source is being used to image the retina; however, when multiple wavelengths of light are used to image different layers of the retina simultaneously, this method is not ideal. This is due to the fact that all of the light sources will change focus together when adjusted using the deformable mirror. Since changes in the focus between retinal layers arise due to location or retinal pathology, it is very difficult to simultaneously maintain the focus of each wavelength on the retinal layer of interest, or to change the focus so that multiple wavelengths could simultaneously be focused on different retinal layers or on the same layer depending upon experimental necessity. The focus of the light can be altered for each light source independently by altering the vergence of the light before entering the optical system. However, for a given defocus, the confocal aperture and PMT detector position must also be changed (in three dimensions) to be placed in the proper position for light detection from the retina. Furthermore, when the focus is changed in this way it alters the amount of light that is coupled into the imaging system. This is an important consideration for imaging the living human eye, as one could increase the fluorescence simply by increasing the power of the excitation light by coupling more light into the system. By altering the focus and the power simultaneously, and monitoring the power of the emitted light to determine the appropriate focus, it remains unknown whether the increase in emission is due to obtaining the appropriate focus or due to simply altering the power of the excitation light. Moreover, visible light can be harmful to the retina and it is important to know how much light one is putting into the eye for safety reasons. If one adjusted the focus of the ingoing light while imaging the eye without simultaneously measuring and adjusting the power of the ingoing light, the retina may be damaged. Accordingly, apparatus and techniques known in the art may be employed for limiting visible light exposure; for example, a shutter under computer control may be used to limit light exposure while the common focusing element and the pinhole translation stage are being manipulated to their desired focus/positions. Alternatively, the source may be electronically modulated. Other approaches are known in the art.

In view of the foregoing, the inventor has recognized the benefits and advantages in providing an enabling solution to address these problems in the form of a method and system for automatically aligning an aperture in an optical system; more particularly, for automatically aligning one or more pin-hole-sized apertures in an optical system having multiple light sources and light detection wavelengths in one or more channels of an optical imaging system, particularly in the presence of at least certain optical aberrations such as, but not limited to, chromatic aberration; and most particularly, for automatic alignment of a confocal aperture in a confocal imaging system such as, but not limited to, a confocal scanning laser microscope or a fluorescence adaptive optics scanning laser ophthalmoscope (FAOSLO), especially for fluorescence imaging in the human eye where the chromatic aberration of the eye under investigation is unknown. The embodied invention enables one to minimize light exposure to the eye and optimize fluorescence excitation and emission detection without altering the amount of light that is put into the eye.

DEFINITIONS AS USED HEREIN

The term 'about' means the amount of the specified quantity plus/minus a fractional amount (e.g., ±10%, ±9%, ±8%, ±7%, ±6%, ±5%, ±4%, ±3%, ±2%, ±1%, ±<1%, etc.) thereof that a person skilled in the art would recognize as typical and reasonable for that particular quantity or measurement.

The term 'substantially' means as close to or similar to the specified term being modified as a person skilled in the art would recognize as typical and reasonable; for e.g., within typical manufacturing and/or assembly tolerances, as opposed to being intentionally different by design and implementation.

SUMMARY

The most general aspects of the invention are a method and associated system for automatically aligning an aperture in an optical system.

An aspect of the invention is a method for automatically aligning a confocal aperture. In an embodiment, the method includes the steps of a) providing an optical imaging system including a first light source having a first wavelength, a respective first confocal imaging system, and a respective first automatically, positionally-adjustable confocal aperture/detector assembly in which there is a fixed separation distance between the confocal aperture and the detector; b) illuminating a reflectance target with the first light source and confocally imaging at least a region of the target; c) using an optimization algorithm to automatically adjust the position of the confocal aperture/detector assembly for obtaining a maximum power measurement of the confocal image; and d) repeating steps (b) and (c) as deemed necessary. According to various exemplary, non-limiting embodiments, the method may include the following additional steps, features, limitations, and/or characteristics:

e) providing a second light source having a second wavelength, a respective second confocal imaging system, and a respective second automatically, positionally-adjustable confocal aperture/detector assembly in which there is a fixed separation distance between the confocal aperture and the detector; f) providing a common focusing element for both the first and second light sources; g) providing a reflectance object to be confocally imaged that is characterized by having chromatic aberration; h) calibrating the optical system such that at least one of the first and the at least second light source has a known focus position; i) setting a fixed focus offset between the first and the at least second light source; j) illuminating the reflectance object with one of the first and the second light sources to generate a fluorescent emission from the reflectance object; k) compensating for an amount of a longitudinal chromatic aberration of the fluorescent emission by translating the second confocal aperture/detector assembly; l) determining a focal plane having a maximum intensity of the fluorescent emission; m) using an optimization algorithm to automatically adjust the position of the second confocal aperture/detector assembly for obtaining a maximum power measurement of the fluorescent emission; and n) repeating steps (k) and (l) as deemed necessary;
  using a Nelder-Mead simplex algorithm;
  wherein the first and the second wavelengths are in a range between 0.45 to 1.2 micrometers;

wherein the common focusing component is a deformable mirror;

wherein determining the focal plane having the maximum intensity of the fluorescent emission comprises using the common focusing component while keeping the confocal imaging system stationary;

further comprising confocally imaging a location in an axial plane of the reflectance object with one of the first and the second wavelengths in reflectance and confocally imaging a location in a different axial plane of the reflectance object with the fluorescent emission from the reflectance object;

wherein the reflectance object is an in-vivo eye.

further comprising compensating for a chromatic aberration of reflected first wavelength light from the in-vivo eye by:

a) adjusting the first confocal imaging system to change the focus of a fluorescence excitation wavelength comprising the first wavelength so that it comes to a focus at a desired target focal plane;

b) repositioning the first automatically, positionally-adjustable confocal aperture/detector assembly using an algorithm under computer control to maximize the first wavelength light throughput at the detector; and c) iterating steps (a) and (b) if desired;

further comprising compensating for a chromatic aberration of fluorescence emission from the in-vivo eye by:

d) repositioning the first automatically, positionally-adjustable confocal aperture/detector assembly using an algorithm under computer control to maximize the fluorescence emission throughput at the detector;

further comprising:

e) using the common focusing element to step through a number of immediately adjacent focal planes of the in-vivo eye;

f) averaging the light at the first detector for an interval at each focal plane;

g) setting the focus to the focal plane with the maximum fluorescence emission;

h) repositioning the first detector using an automated algorithm under computer control to maximize throughput at the detector; and i) iterating steps (e-h) as desired;

further comprising:

j) adjusting the second confocal imaging system such that the second wavelength light is focused on a desired focal plane of the in-vivo eye;

k) repositioning the second detector using an automated algorithm under computer control to maximize the second wavelength light throughput at the second detector; and l) iterating steps (j) and (k) as desired.

An aspect of the invention is an optical system. In an embodiment, the optical system includes an optical imaging system including a first light source having a first wavelength; a respective first confocal imaging system; a respective first automatically, positionally-adjustable confocal aperture/detector assembly in which there is a fixed separation distance between the confocal aperture and the detector; a second light source having a second wavelength; a respective second confocal imaging system; a respective second automatically, positionally-adjustable confocal aperture/detector assembly in which there is a fixed separation distance between the confocal aperture and the detector; a common focusing element for the first light source and the second light source; and a control mechanism operatively coupled to at least one of the first confocal imaging system, the second confocal imaging system, the first automatically, positionally-adjustable confocal aperture/detector assembly, the second automatically, positionally-adjustable confocal aperture/detector assembly, and the common focusing element. According to various exemplary, non-limiting embodiments, the optical system may include the following additional components, assemblies, features, limitations, and/or characteristics:

further comprising a wavefront sensor operatively coupled to the optical system;

wherein the wavefront sensor is operatively coupled to the control mechanism;

wherein the first and the second wavelengths are in a range between 0.45 to 1.2 micrometers;

wherein one of the first and the second wavelengths is in a visible spectrum and suitable for stimulating a fluorescence emission from an object to be imaged, further wherein one of the second and the first wavelengths is in an infrared spectrum;

wherein the common focusing element is a deformable mirror;

further comprising a third light source having a third wavelength, wherein the wavefront sensor is disposed to receive the third wavelength light.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

The reference numerals depicted in FIG. 1 refer to the same respective elements or components in FIGS. 2-6, in which figures the components are not numbered for the sake of clarity of the diagram.

DETAILED DESCRIPTION OF NON-LIMITING, EXEMPLARY EMBODIMENTS

Figure 1:
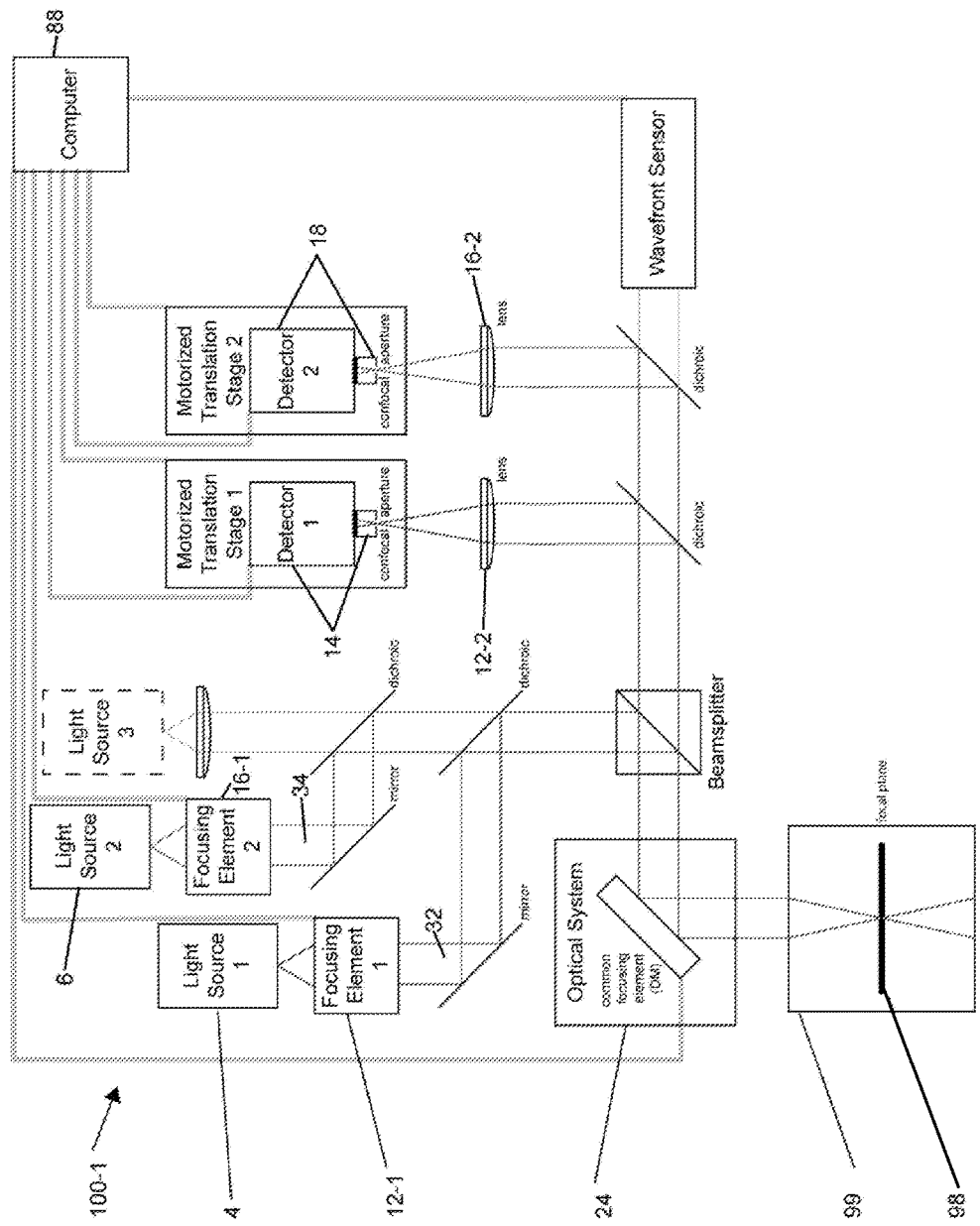
FIG. 1 schematically illustrates an optical system for multi-wavelength imaging of a reflectance target without chromatic aberration, according to an illustrative aspect of the invention.

The embodied invention is conveniently illustrated within the context of the imaging work described as follows.

Participants

Participants with AMD were recruited from the faculty practice of the Flaum Eye Institute at the University of Rochester Medical Center. Normal controls were recruited from the University of Rochester community. All participants were phakic. All participants gave written informed consent after the nature of the research and possible risks were explained both verbally and in writing. All experiments were approved by the Research Subjects Review Board of the University of Rochester and adhered to the tenets of the Declaration of Helsinki.

Clinical Imaging

Color fundus photography was performed on all participants. Patients underwent further clinical imaging using commercial cSLO (Spectralis HRA+OCT, Heidelberg Engineering, Germany). cSLO images (field of view: 30°×30°) were obtained in both infrared reflectance and FAF imaging modes. FAF images were acquired on separate days from AO fluorescence imaging to limit cumulative daily visible light exposures. FAF images were used to assess the overall pattern of RPE fluorescence and in some cases to guide imaging sessions to areas of interest.

FAOSLO Imaging

We used a broadband FAOSLO nearly identical in optical design to one described in detail in A. Dubra and Y. Sulai, "Reflective afocal broadband adaptive optics scanning ophthalmoscope," Biomed. Opt. Express 2(6), 1757-1768 (2011), which is incorporated by reference in its entirety. Only relevant system parameters and the modifications to the light delivery and detection portions of the system that were made to implement the embodied method will be discussed in detail. The size of the FAOSLO imaging field subtended ~1.5°×1.5° on the retina and image sequences were acquired at ~20 Hz. For AF imaging, three wavelengths of light were simultaneously delivered for wavefront sensing, infrared (IR) imaging, and fluorescence excitation. Wavefront sensing used an 847 nm laser diode (QFLD-850-10SB-PM, QPhotonics, LLC, Ann Arbor, Mich., USA), IR reflectance imaging used a 796 nm (14 nm FWHM) superluminescent diode (Inphenix, Inc., Livermore, Calif.), and fluorescence excitation was stimulated using a 532 nm laser diode module (FiberTec II, Blue Sky Research, Milpitas, Calif.).

To ensure stable power output of the 532 nm excitation source, a fiber-coupled feedback collimator (FiberTec II Fiber Feedback Collimator (FFC), Blue Sky Research, Milpitas, Calif.) was used; the FFC provided ~0.5% power stability (manufacturer specification). A computer controlled electronic shutter (04IE5211, CVI Melles-Griot, Rochester, N.Y., USA) placed in front of the FFC controlled visible light exposure duration. We used a long working distance 20× microscope objective (ULWD CDPlan20, Olympus Corporation, Tokyo, Japan) to expand the unduly small collimated 1.37 mm beam that emerged from the FFC. The microscope objective focused the light onto a 5 μm aperture; this spatially filtered the light and effectively produced a point source for illumination. Light emerging from the spatial filter was focused using an 80 mm focal length positive achromatic lens (Linos G0631430000, Qioptiq, Inc., Fairport, N.Y., USA). The achromatic lens was mounted onto a motorized translation stage (MTS-50, Thorlabs, Newton, N.J., USA) so that the vergence of the light at the entrance pupil could be precisely controlled; details on dual focus settings and automation for optimizing LCA compensation are provided below. When placed at its collimated position, the diameter of the beam that emerged filled the entire lens (22 mm). The beam profile was approximately Gaussian; an aperture at the entrance pupil of the system allowed only the central 7.25 mm portion of the beam into the instrument.

Wide Field Fundus Image Guided Targeting

We used a computer controlled fixation target to position the FAOSLO imaging field to specific retinal locations. The target was typically a white circle (the size was varied depending upon the visual acuity of the patient) that was projected onto the ceiling using a DLP projector and viewed off an anti-reflection coated laser window (W1-IF-3050-C-633-1064-45UNP, CVI Melles-Griot, Rochester, N.Y., USA) placed in front of the eye. The fixation target was produced and controlled with a custom MATLAB (MathWorks, Natick, Mass., USA) graphical user interface (GUI). The target stimulus was generated and controlled using elements of the Psychophysics toolbox extensions reported in D. H. Brainard, "The psychophysics toolbox," Spat. Vis. 10(4), 433-436 (1997); M. Kleiner, D. Brainard, and D. G. Pelli, "What's new in Psychtoolbox-3?" Perception 36, (2007); and D. G. Pelli, "The VideoToolbox software for visual psychophysics: Transforming numbers into movies," Spat. Vis. 10(4), 437-442 (1997), the subject matters of which are incorporated by reference in their entireties.

The GUI allowed loading in a wide field fundus image obtained with a clinical instrument (such as a fundus photograph or cSLO image), calibrate the magnification and offset for the location of the FAOSLO imaging field, and then use the software to target specific locations using the fundus image as a map. Vascular features in the wide field fundus image were compared to those in the live AO IR reflectance image to ensure that the patient was fixating on the target and that the mapping between images was accurate. A small square overlaid on the fundus image displayed in the GUI indicated the location being targeted; as the fixation target and thus the observer's eye were moved, this mark moved across the wide field fundus image. The GUI communicated through a network connection to the image recording software that ran on a separate PC and automatically marked recorded locations on the fundus image whenever an image sequence was acquired. This provided feedback as to which locations had been imaged, preventing repeat imaging of the same location (and thus overexposure to visible light). The GUI displayed the retinal coordinates of each location and saved the coordinates to a text file as each image sequence was acquired. At the end of each imaging session, the fundus image, with each recording location marked as an overlaid square, was saved; these images were later used as a guide (along with the text file of recording coordinates) for montaging of images and to map FAOSLO images to their corresponding locations on wide field fundus images. For many participants, the projected stimulus was too dim for them to see when the fluorescence excitation light came on; in those cases a laser pointer was pointed at the projected target on the screen to provide a brighter target for fixation.

Light Safety

Light source power levels and exposure durations were used that were well below the maximum permissible exposure (MPE) specified by the American National Standards Institute (ANSI) standard for the Safe Use of Lasers, ANSI Z136.1-2007 [24]. We used ~14 μW of 847 nm light for wavefront sensing, ~140 μW of 796 nm light for infrared imaging, and 35-40 μW of 532 nm light for fluorescence excitation. Powers were kept constant and exposure durations were limited to ensure safety. We stayed below the Rochester Exposure Limit (REL) [25], which is partially based on the ANSI but is much more conservative, especially in the visible wavelength range. We developed the photochemical REL based on previous data from Morgan et al. that showed changes in monkey RPE AF after exposure to visible light levels below the ANSI limit. The REL software calculations ensured that the combined exposure to all three wavelengths simultaneously was safe; the calculations it performs are based on published methods for calculating contributions for multi-wavelength ocular exposures. We used a custom software program to calculate the REL before each imaging session as reported in E. A. Rossi and J. J. Hunter, Rochester Exposure Limit Calculator [Computer software] (University of Rochester, 2013) (http://aria.cvs.rochester.edu/software/RELcalculator.html), the subject matter of which is incorporated by reference in its entirety. For 40 μW, the REL specified that the maximum duration of 532 nm light exposure at any given retinal location was ~120 seconds (~22 times lower than the ANSI MPE). This power and exposure duration resulted in retinal radiant exposures less than 2.44 J/cm$^2$, the ANSI "blue light hazard" for the range 400-450 nm. The visible light appeared bright but was well tolerated by the patients and controls. We exposed a single location to all three light sources simultaneously for ~90 seconds. Since we used ~75% our full exposure duration at each location imaged, we used our fixation target software and vascular landmarks to ensure that each imaging location was spaced sufficiently from adjacent imaging locations so that fixational drifts or microsaccades did not cause exposure locations to overlap. The IR light levels used could be viewed continuously for the maximum duration specified by ANSI Z136.1-2007 (30,000 seconds). We imaged a single location for a maximum of ~5 minutes using just the infrared light sources, so the total infrared exposure duration was ~7 minutes at each location (~10 and ~124 times lower than the ANSI MPE for the IR and wavefront sensing light sources, respectively).

Dual-focus, Fixed Offset Procedure

To maximize data collection efficiency, we simultaneously acquired images of the photoreceptor layer in IR and of the RPE in fluorescence. The IR light was focused on the photoreceptors, while the fluorescence excitation light was focused on the RPE. The focus of the photoreceptor and RPE layers may advantageously be very close to one another axially, as the photoreceptor outer segments are in contact with the apical processes of the RPE cells. If each wavelength were to enter the eye collimated, longitudinal chromatic aberration (LCA) would cause the longer wavelength of light to focus deeper than the shorter wavelength. Therefore, an appropriate amount of focus offset between the two sources must be achieved to cause them to focus at the same axial position.

Ultimately, since the wavelength of fluorescent light emitted from the lipofuscin in the RPE is different than the wavelength used for fluorescence excitation (e.g., first light source 4 at 532 nm), the respective confocal aperture should be placed appropriately for the emission bandwidth of the fluorescence emission filter. All of this positioning must be done appropriately to compensate for the chromatic aberration of the eye and obtain in-focus images of the RPE.

We started by setting a fixed focus offset that minimized LCA based upon published measures. We set this fixed focus offset by getting each source 4, 6 in focus in reflectance imaging mode on a model eye with no chromatic aberration, which consisted of a lens and a piece of paper upon which many small (9.9 μm diameter) fluorescent beads (FS06F, Bangs Laboratories, Inc., Fishers, Ind., USA) had been deposited. We began by making the 532 nm light 32 collimated using a shear plate. We then manually adjusted the focus of the light using the common focusing element 24 (e.g., a deformable mirror) to bring the image of the paper into sharp focus. The position of the first confocal aperture/detector assembly 14 was then adjusted to maximize throughput. We used a large confocal aperture (~3.4 times the Airy disc diameter at 650 nm), and iterated between adjusting the focus using the common focusing element 24 and adjusting the first confocal aperture position until the best subjective image quality was achieved.

The next step was to place the first confocal aperture to maximize the detection of the fluorescence emission light that would be emitted by the RPE. An emission filter was placed in front of the PMT detector so that we could visualize the fluorescent beads. To maximize light collection across the bandwidth of lipofuscin emission, we used a filter with a broad band pass (150 nm) centered at 650 nm (BrightLine FF01-650/150-25, Semrock, Inc., Rochester, N.Y., USA). After the filter was placed, pinhole positioning was done using the automated method described below. Once the fluorescence channel was set, the IR channel (second light source 6) was adjusted to obtain an in focus image of the paper (in reflectance). This was done by translating the tip of the fiber of the 796 nm SLD (which was mounted on a manual micrometer) and adjusting both the axial position of the lens in front of the second confocal aperture and the lateral position of the confocal aperture iteratively until the best subjective image of the paper was obtained. This procedure would have been sufficient for configuring the system for AF imaging if the eye did not have any chromatic aberration. However, if adjustments were not made to compensate for the chromatic aberration of the eye, when the 796 nm light was focused on the photoreceptors, the 532 nm fluorescence excitation light would be focused on the inner retina.

As a first step towards LCA compensation, we used published measurements of the LCA of the human eye to determine the dioptric difference in focus (or vergence) needed to compensate for this LCA. We used the dioptric difference between the 532 nm excitation wavelength and 796 nm reflectance wavelength to calculate the vergence offset needed for the ingoing light and the difference between the reflectance wavelength and the center of the emission band pass filter (650 nm) to determine the outgoing LCA compensation needed. The ingoing 532 nm light was defocused 0.99 D by translating the lens in front of the spatial filter 9 mm. The LCA compensation for the outgoing light (0.36 D) was made by translating the confocal aperture 3.74 mm. We calculated the distances required to move these elements to achieve the desired focus offsets using a simple geometrical optics model of the system, which took into account the distances between the collimating lens and entrance pupil (~330 mm), system magnification (1.067), and focal lengths of lenses at the source (80 mm) and detector (100 mm). We ensured that the movements we made were precise and repeatable by controlling each with optically encoded piezoelectric actuators (MTS-50 for the collimating lens and Z812B for the detector; Thorlabs, Inc., Newton, N.J., USA).

Automatic Focus Refinement

The focus offset procedure outlined above brought us close to achieving the desired LCA compensation; however, in practice we found that the best focus was usually slightly different from these fixed offsets for each individual. A solution to this problem was to acquire several different image sequences at multiple foci, with the hope that one of them would be in focus. Since we were limited to only 120 seconds at each location, and it took ~20-30 seconds to obtain enough frames to generate a high signal to noise ratio image of the RPE, this method only allowed perhaps 3-4 different foci to be obtained. As the appropriate focus was unknown, this method was inefficient and impractical and often the best focus was never obtained in the few attempts we had at each location. It was clear from these early experiments that a small amount of chromatic aberration remained that needed to be compensated for. We therefore developed an automated procedure to determine the focus that gave the highest intensity fluorescence signal.

As previously mentioned, an algorithmic method for true auto focusing (i.e., one that used an objective image quality metric) could not be used, as each frame in the image contained too little signal to provide a meaningful measurement. However, small focus differences do result in quantifiable changes in fluorescence intensity. These small changes in intensity resulting from small differences in focus are very difficult to appreciate with the naked eye, but can be quantified reliably using a computer algorithm. We used an approach to determine the focus with peak fluorescence intensity. The deformable mirror (24), under computer (88) control, was used to step through several different foci around the defocus setting that gave the best cone image in the reflectance imaging channel (2). At each foci, a small number of frames were acquired (~5-10); the mean pixel value was computed for each frame and then the average was computed for all frames acquired at that focus. Typically, a fixed number of frames were averaged at each interval, although this varied as we refined the process to use fewer frames. In our early experiments, we kept the shutter open during this entire process (~30 seconds); however, we found that it took a second or two of software and hardware latency for the focus shape to be placed on the DM and the AO to converge. In our later implementations, we closed the shutter between each focus interval. This minimized light exposure during the automated focus procedure to ~10 seconds, allowing more of the limited exposure duration at each location to be used for imaging.

Automatic Confocal Aperture Alignment

The automatic focus refinement procedure described above allowed us to find the focus needed to obtain the highest fluorescence signal. However, the chromatic aberration of the fluorescent light still required refinement. Because we used a relatively large pinhole, and a broad band pass filter, we were much less sensitive to LCA on the detection side. Transverse chromatic aberration (TCA), however, remained a problem. The TCA of the eye and system between the excitation and emission wavelengths causes the focused spot at the confocal aperture to be displaced laterally relative to where it was on the model eye. TCA causes a slight lateral misalignment of the confocal aperture when the human eye is imaged. TCA can arise due to either the system or the eye, or both. Additionally, as the human eye moves and the pupil position changes, the TCA changes as well. Grieve and colleagues (K. Grieve et al., "Multi-wavelength imaging with the adaptive optics scanning laser ophthalmoscope," Opt. Express 14, 12230-12242 (2006)) measured the TCA between 532 nm and 658 nm using an AOSLO and found a range of 48-142 arc seconds; they also measured TCA variation across the central 2.5 mm of the pupil and found that it varied by 100 arc seconds. Since the confocal aperture is large, we still get some signal through in these misaligned positions, but we found that we could greatly improve signal throughput if we adjusted the confocal aperture slightly to optimize signal intensity. This was impossible to do manually, as we needed to optimize the pinhole position based upon very small intensity fluctuations and by making extremely small movements of the aperture, all in a relatively short time with the eye constantly in motion (which also caused small fluctuations in single frame intensities). However, we found that this problem was solvable with an automated algorithmic control method.

Algorithmic methods can be employed to solve the problem of optimizing light coupling into an optical system. One algorithm that has been successfully employed for this purpose is the Nelder-Mead optimization algorithm, as reported in J. A. Nelder and R. Mead, "A Simplex Method for Function Minimization," Comput. J. 7(4), 308-313 (1965). Our detector assemblies were motorized and the Nelder-Mead optimization algorithm was implemented using functions from the MATLAB program NELDER_MEAD as reported in J. Borggaard, NELDER_MEAD [Computer software] (2009), http://people.sc.fsu.edu/~jburkardt/m_src/nelder_mead/nelder_mead.html, the subject matter of both of the references incorporated by reference in their entireties. The PMT was mounted on a three-axis translation stage (RB13, Thorlabs Inc., Newton, N.J.) and each axis was equipped with an optically encoded piezoelectric actuator (Z812B, Thorlabs Inc., Newton, N.J.). These actuators allowed for extremely small movements (0.05 µm) to be made under computer control by interfacing the motors using the APT control software extensions (Thorlabs, Inc., Newton, N.J.), which was implemented in a MATLAB control GUI. The distance between the aperture and detector was fixed by attaching the confocal aperture to the PMT using a lens tube, so they moved together in three dimensions. The implementation of the Nelder-Mead algorithm was validated using a model eye by measuring the intensity of the signal at the detector for a matrix of points around the point spread function. We did this for both the model eye in reflectance using a ~1.2 Airy disc pinhole (20 um at 532 nm) and in fluorescence using the ~3.4 Airy disc pinhole (75 um at 650 nm). We used these setups to test different algorithm constants, such as the tolerance, which determined simplex convergence, and to determine the search space required to optimize Nelder-Mead performance. Algorithm performance was characterized for randomly determined starting positions whose locations were generated using the rand command in MATLAB.

Dual-registration

We used a published dual registration method to register the AF images using the motion from the IR reflectance channel. Briefly, this method uses cross-correlation to register the reflectance IR images and applies the calculated motion shifts to the AF images. Registered images were then averaged to obtain a high signal to noise ratio image; we typically averaged around 1160 autofluorescence images to obtain an image of the RPE cell mosaic. For efficiency, we used the data from both the forward and backward scans; the sinusoidal distortion from the resonant scan pattern was removed and forward and backward scan images were interleaved prior to registration. We used in-house software (A. Dubra and Z. Harvey, "Registration of 2D Images from Fast Scanning Ophthalmic Instruments," in Biomedical Image Registration, B. Fischer, B. M. Dawant, and C. Lorenz, eds., Lecture Notes in Computer Science No. 6204 (Springer Berlin Heidelberg, 2010), pp. 60-71) to perform strip-based registration.

FIGS. 1-6 successively schematically illustrate aspects of the embodied method and apparatus. Common reference numerals for common elements are used throughout the figures. Drawings are not to scale.

FIG. 1 schematically illustrates an optical system 100-1 for multi-wavelength imaging of a reflectance target 99 (reference target) without chromatic aberration. Both wavelengths 32 from the first light source 4 and 34 from the second light source 6 come to a focus at the same position onto the target focal plane 98 after entering the target medium 99 because there is no chromatic aberration, and thus both wavelengths focus at their respective confocal apertures in confocal aperture/detector assemblies 14, 18. Note that in FIGS. 1-6, focusing element 12-1 and lens 12-2 comprise the first confocal imaging system and focusing element 16-1 and lens 16-2 comprise the second confocal imaging system. Note that despite the fact that the rays entering the system appear parallel in this drawing, each wavelength of light will enter the system with an amount of vergence that is necessary to bring each in focus on the target.

Figure 2:
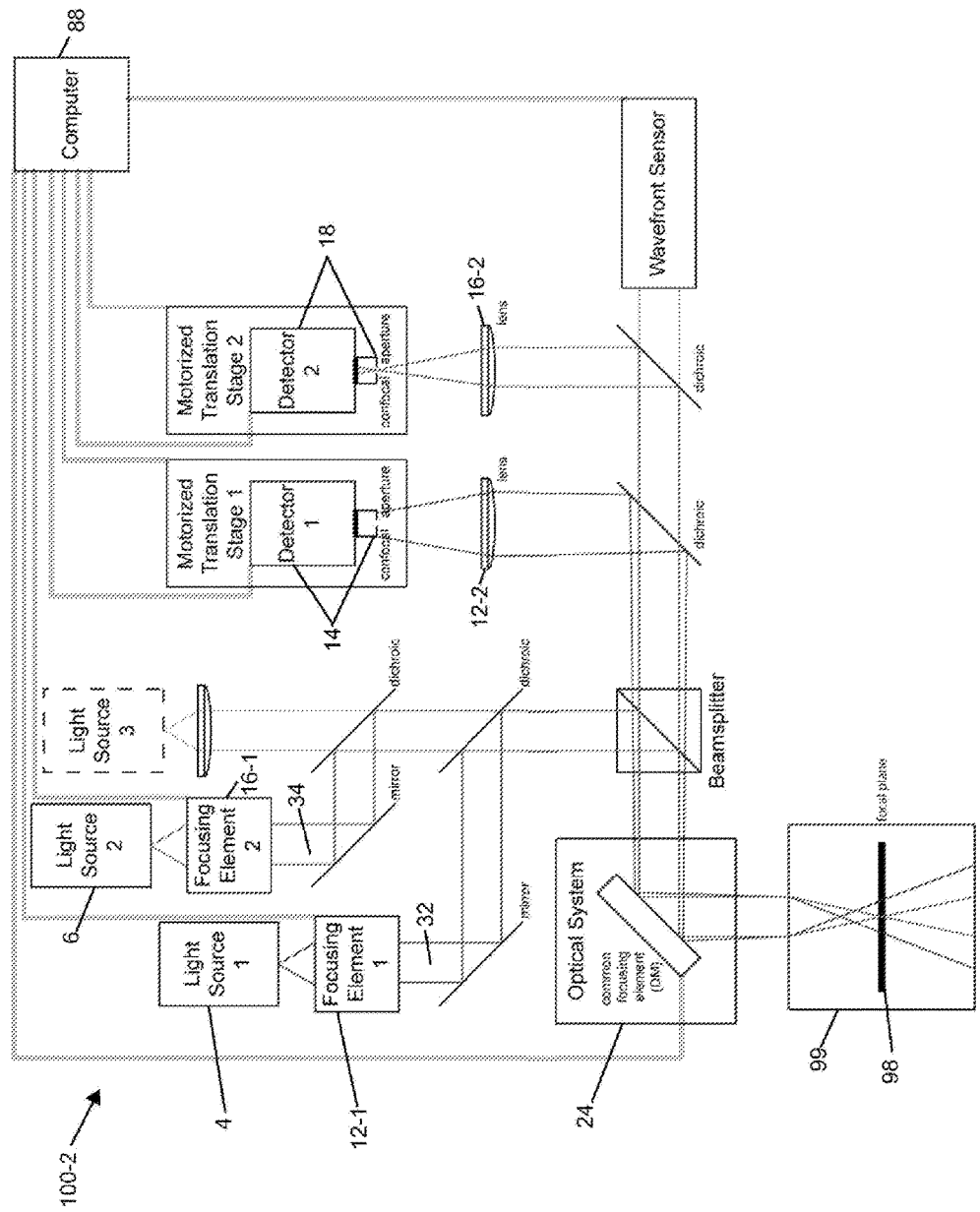
FIG. 2 schematically illustrates an optical system with multi-wavelength imaging of a reflectance target with uncompensated chromatic aberration, according to an illustrative aspect of the invention.

FIG. 2 illustrates an optical system 100-2 for multi-wavelength imaging of a reflectance target 99 (e.g., an in-vivo-eye) with uncompensated chromatic aberration. Each wavelength 32, 34 focuses at a different axial position within the target medium 99 due to the fact that the shorter wavelength (32) is refracted more by the target medium than the longer wavelength (34), due to chromatic aberration of the target medium (e.g., in-vivo-eye). This alters the focus causing the light to no longer come to a focus at the confocal aperture 14.

Figure 3:
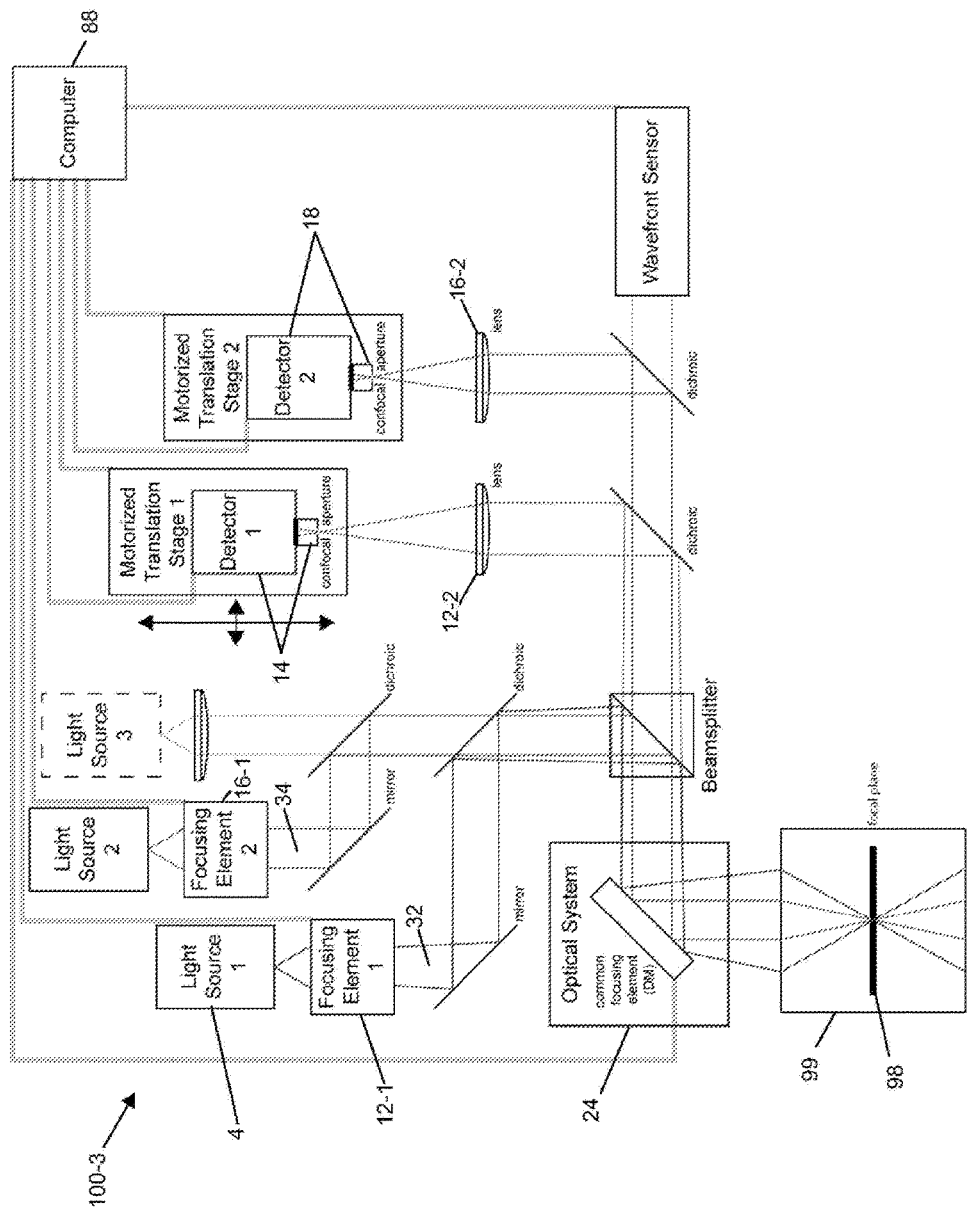
FIG. 3 schematically illustrates an optical system with multi-wavelength imaging of a reflectance target with a common focal plane and compensation for chromatic aberration, according to an illustrative aspect of the invention.

FIG. 3 schematically illustrates an optical system 100-3 with multi-wavelength imaging of a reflectance target with a common focal plane and compensation for chromatic aberration.

Chromatic aberration compensation allows both wavelengths 32, 34 to focus in the target medium at the same focal plane. Chromatic aberration is compensated for by:
1) adjusting focusing element 1 (12-1), to change the focus of the fluorescence excitation wavelength 32 before it enters the system so that it comes to a focus at the target focal plane 98;
2) repositioning detector 1 (14) with motorized translation stage 1, under computer (88) control, using an automated algorithm (e.g., the Nelder-Mead algorithm) to maximize throughput at the detector 14; and
3) optionally, iterating between steps (1) and (2).

Figure 4:
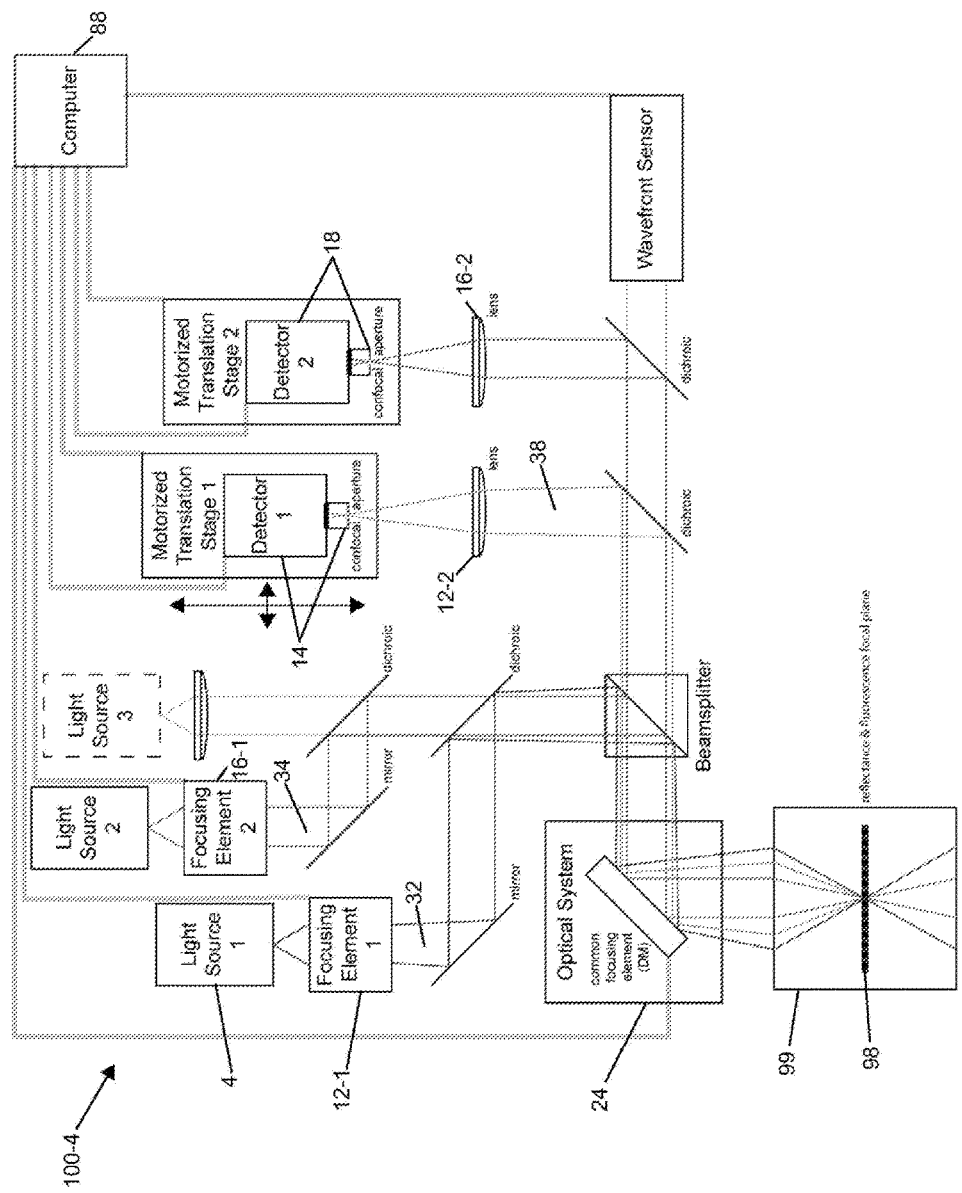
FIG. 4 schematically illustrates an optical system with multi-wavelength imaging of both a fluorescence and reflectance target at a common focal plane with compensated chromatic aberration, according to an illustrative aspect of the invention.

FIG. 4 schematically illustrates an optical system 100-4 with multi-wavelength imaging of both a fluorescence and reflectance target at a common focal plane with compensated chromatic aberration. As in configuration 100-3, chromatic aberration compensation for the ingoing light allows both the reflectance imaging wavelength (34) and the fluorescence excitation wavelength (32) to focus in the target medium 99 at the same focal plane 98. Chromatic aberration compensation for the outgoing light allows the emitted fluorescent light (38) to come to a focus at the position of the confocal aperture of detector assembly 14. Chromatic aberration is compensated by repositioning detector 1 (14) with motorized translation stage 1, under computer (88) control, using an automated algorithm (e.g., Nelder-Mead algorithm) to maximize throughput at the detector.

Figure 5:
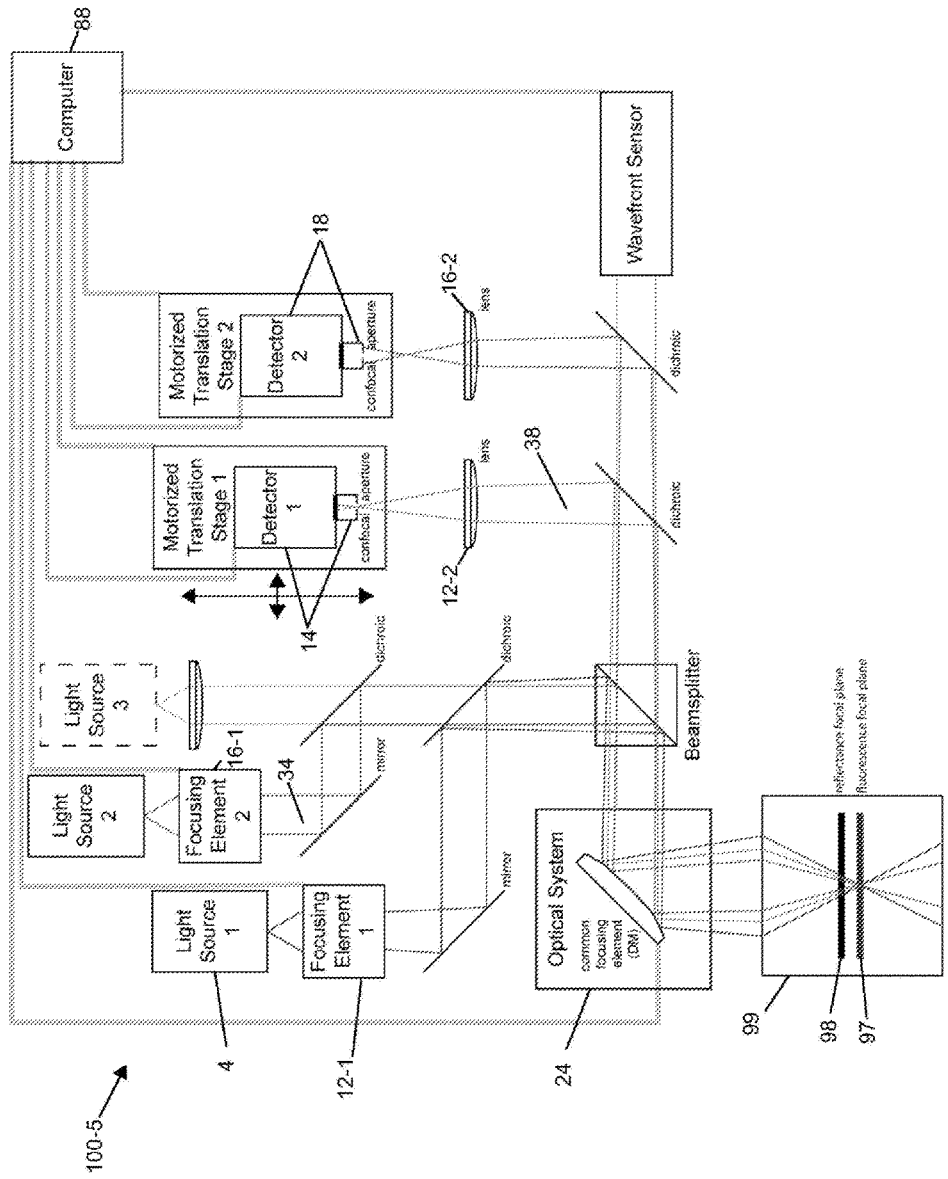
FIG. 5 schematically illustrates an optical system with multi-wavelength imaging of both a fluorescence and reflectance target at different focal planes with compensated chromatic aberration and refinement of focus for fluorescence imaging by use of a common focusing element, according to an illustrative aspect of the invention.

FIG. 5 schematically illustrates an optical system 100-5 with multi-wavelength imaging of both a fluorescence and reflectance target at different focal planes with compensated chromatic aberration and refinement of focus for fluorescence imaging by use of a common focusing element. As in configuration 100-4, chromatic aberration compensation for the ingoing light allows both the reflectance imaging wavelength (34) and the fluorescence excitation wavelength (32) to focus in the target medium 99 at the same focal plane 97. However, in this case the reflectance (98) and fluorescence (97) focal planes are at different axial positions. The common focusing element 24 is adjusted to maximize fluorescence emission (38) by adjusting the focus of the ingoing light to the fluorescence focal plane 97. The common focusing element 24 is advantageously used for this step because it does not change the amount of light entering the target medium 99. If the focusing element 1 for light source 1 were used instead, it would change the amount of fluorescence excitation light 32 entering the system and thus reaching the target. This could cause the fluorescence 38 from the sample to increase simply due to the fact that the amount of excitation light was increased. By using the common element 24, the axial position of the focus of the light changes within the target medium but the overall power of the incident light does not change. This is accomplished by:
1) using the common focusing element 24 (e.g., a deformable mirror (DM)) to step through a number of immediately adjacent focal planes;
2) averaging the light at the detector 14 for an interval at each focal plane;
3) setting the focus to the focal plane with the maximum fluorescence emission;
4) repositioning detector 1 (14) with motorized translation stage 1, under computer (88) control, using an automated algorithm (e.g., the Nelder-Mead algorithm) to maximize throughput at the detector; and
5) optionally, iterating between steps (1-4).

Note that the common focusing element changes the focus of both the fluorescence excitation light and the reflectance imaging light. This causes the reflectance beam to be out of focus.

Figure 6:
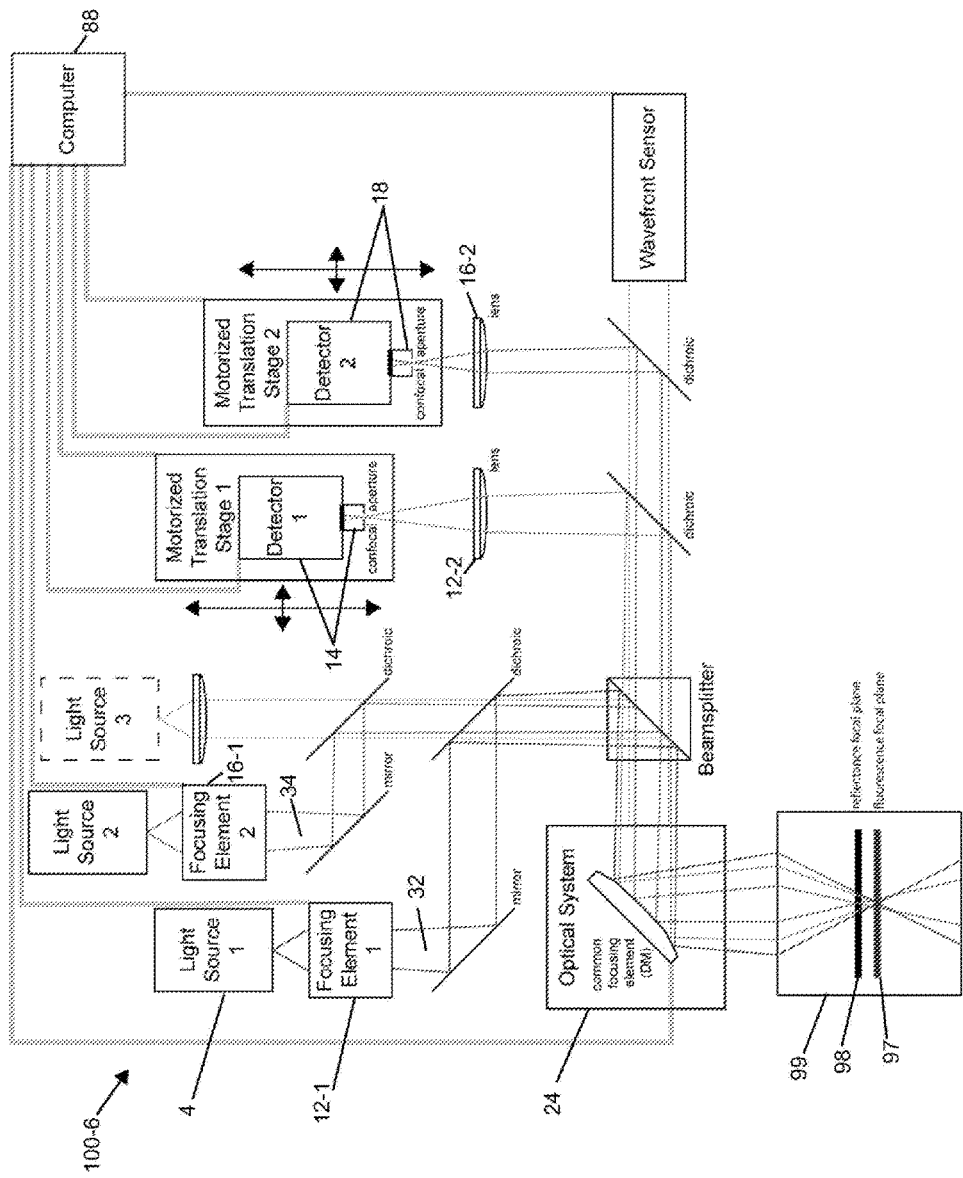
FIG. 6 schematically illustrates an optical system with multi-wavelength imaging of both a fluorescence and reflectance target at different focal planes with compensated chromatic aberration and refinement of focus for fluorescence imaging with a common focusing element and compensatory adjustment of the reflectance light source, according to an illustrative aspect of the invention.

FIG. 6 schematically illustrates an optical system 100-6 with multi-wavelength imaging of both a fluorescence and reflectance target at different focal planes with compensated chromatic aberration and refinement of focus for fluorescence imaging with a common focusing element and compensatory adjustment of the reflectance light source. This is a modification of configuration 11-5 that is necessary to bring the reflectance imaging light into focus at the reflectance focal plane after the focus has been adjusted using the common focusing element to maximize fluorescence. This is accomplished by:
1) adjusting focusing element 2 (16-1) such that the ingoing reflectance imaging wavelength 34 is focused on the reflectance focal plane 98;
2) repositioning detector 2 (18) with motorized translation stage 2, under computer (88) control, using an automated algorithm (e.g., the Nelder-Mead algorithm) to maximize throughput at the detector; and
3) optionally, iterating between steps (1) and (2).

Results

The Nelder-Mead simplex algorithm performed well when tested on a model eye, both in reflectance and in fluorescence. Results in humans showed that the algorithm was in most cases able to increase the signal substantially, but that the change in intensity varied depending on the starting position. In some cases the confocal aperture was close to the optimal location, so the increase in intensity was negligible, in other cases it was far from its optimal location and we saw increases of up to a factor of 10 in intensity. This variability in the starting position makes it difficult to quantify the performance in an objective way. The greatest intensity increase was usually observed during the first run of the Nelder-Mead algorithm, as the starting position for this run was from the position that the confocal aperture was set to on the model eye. The Nelder-Mead algorithm sometimes did not converge during the 30 second exposures that we typically used. This was often due to the Nelder-Mead tolerance variable being too low for the algorithm to reach convergence. In these cases we either chose the position setting with the highest intensity during that run or reset it to the value from the previous run.

The focusing method proposed here has provided us with the first in vivo images of individual RPE cells in AMD. The images we obtained look very similar to those seen in post mortem histology images from AMD donor eyes, RPE imaging in FAOSLO in patients with AMD remains challenging. Improvements that we anticipate will further increase performance are eye tracking based image stabilization and the use of achromatizing lenses. Eye tracking and stabilization of the imaged area will allow for a more controlled light exposure and more uniform signal to noise ratio in the registered image average. Currently, as the eye moves around, the locations on the edge of the frame drift in and out of the imaging field. An appropriately designed achromatizing lens placed at the exit pupil of the system could potentially also improve performance. We used a broad band emission filter here to increase our fluorescence signal, but this causes the light distribution at the detector to elongate axially along the path of the beam as each wavelength focuses at different positions. An achromatizing lens can make this light distribution more compact, causing the light emitted at different wavelengths from individual lipofuscin granules to focus at the same position axially. This should improve both axial resolution and throughput.

This method might be further optimized by the use of higher light levels, such as those used by Morgan et al. (2009), and permitted under the current ANSI standard. This could potentially allow images to be obtained more rapidly and/or facilitate the use of a smaller confocal aperture that could improve resolution. However, we chose to use very conservative light levels here for two main reasons. The first is our concern for patient safety, particularly for the AMD retina, which may be more susceptible to damage from visible light exposures. The second is that the ANSI standards will soon be updated based upon new data, and the forthcoming standards will be more conservative.

Many of the images we obtained in AMD eyes appeared to be in focus, but did not contain structure indicative of individual cells, particularly in areas that already have detectable lesions. This makes interpretation of these images difficult as it remains ambiguous as to whether the cellular features were not present due to our inability to image them or if they are truly absent. This is a familiar problem for those using in vivo imaging methods. Many of the RPE cell morphologies seen in the later stages of AMD, such as multilayered cells and heaping and sloughing of cells could disrupt our ability to see cellular structure. The AF imaging technique in FAOSLO capitalizes on the fact that the normal RPE is arranged in a flat monolayer. It is thought that the contrast arises due to the nucleus of the cell providing contrast to the bright lipofuscin laden surround (this has not been confirmed however). When the RPE is disrupted in disease it is not clear if we might expect to see any contrast between the center and surround of the cell using this imaging method. Additionally, data is needed to distinguish normal changes related to aging from disruptions related to disease in FAOSLO images of the RPE cell mosaic. One surprising finding is that RPE morphology was disrupted in areas that have relatively normal appearing RPE fluorescence in conventional commercial cSLO FAF images. This demonstrates that despite a uniform fluorescence signal in low resolution imaging, the underlying RPE morphology can be irregular. Further work is needed to characterize how these changes in the RPE mosaic relate to the changes to photoreceptors seen in reflectance FAOSLO images and the overall pattern of fluorescence seen in cSLO FAF images.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

I claim:

1. A method for automatically aligning a confocal aperture, comprising:
   a) providing an optical imaging system including: a first light source having a first wavelength, a respective first confocal imaging system, and a respective first automatically, positionally-adjustable confocal assembly including a first confocal aperture and a first detector, wherein there is a fixed separation distance between the first confocal aperture and the first detector, the first detector is mounted on a first translation stage such that the first confocal aperture and the first detector are moved together by the first translation stage, and the first confocal assembly is automatically, positionally-adjustable relative to the first confocal imaging system by the first translation stage;
   b) illuminating a reflectance target with the first light source and confocally imaging at least a region of the target;
   c) using the first translation stage and an optimization algorithm to automatically adjust the position of the first confocal assembly relative to the first confocal imaging system for obtaining a maximum power measurement of the confocal image;
   e) providing a second light source having a second wavelength, a respective second confocal imaging system, and a respective second automatically, positionally-adjustable confocal assembly including a second confocal aperture and a second detector, wherein there is a fixed separation distance between the second confocal aperture and the second detector, the second detector is mounted on a second translation stage such that the second confocal aperture and the second detector are moved together by the second translation stage, and the second confocal assembly is automatically, positionally-adjustable relative to the second confocal imaging system by the second translation stage;
   f) providing a common focusing element for both the first and second light sources;
   g) providing a reflectance object to be confocally imaged that is characterized by having chromatic aberration;
   h) calibrating the optical system such that at least one of the first and the at least second light source has a known focus position;
   i) setting a fixed focus offset between the first and the at least second light source;
   j) illuminating the reflectance object with one of the first and the second light sources to generate a fluorescent emission from the reflectance object;
   k) compensating for an amount of a longitudinal chromatic aberration of the fluorescent emission by translating the second confocal assembly;
   l) determining a focal plane having a maximum intensity of the fluorescent emission; and
   m) using the second translation stage and an optimization algorithm to automatically adjust the position of the second confocal assembly relative to the second confocal imaging system for obtaining a maximum power measurement of the fluorescent emission.

2. The method of claim 1, comprising using a Nelder-Mead simplex algorithm.

3. The method of claim 1, wherein the first and the second wavelengths are in a range between 0.45 to 1.2 micrometers.

4. The method of claim 1, wherein the common focusing component is a deformable mirror.

5. The method of claim 1, wherein determining the focal plane having the maximum intensity of the fluorescent emission comprises using the common focusing component while keeping the confocal imaging system stationary.

6. The method of claim 1, further comprising confocally imaging a location in an axial plane of the reflectance object with one of the first and the second wavelengths in reflectance and confocally imaging a location in a different axial plane of the reflectance object with the fluorescent emission from the reflectance object.

7. The method of claim 6, wherein the reflectance object is an in-vivo eye.

8. The method of claim 7, further comprising compensating for a chromatic aberration of reflected first wavelength light from the in-vivo eye by:
   (1) adjusting the first confocal imaging system to change the focus of a fluorescence excitation wavelength comprising the first wavelength so that it comes to a focus at a desired target focal plane; and
   (2) repositioning the first automatically, positionally-adjustable confocal aperture/detector assembly relative to the first confocal imaging system using an algorithm under computer control to maximize the first wavelength light throughput at the first detector.

9. The method of claim 8, further comprising compensating for a chromatic aberration of fluorescence emission from the in-vivo eye by:
   (3) repositioning the first automatically, positionally-adjustable confocal aperture/detector assembly relative to the first confocal imaging system using an algorithm under computer control to maximize the fluorescence emission throughput at the first detector.

10. The method of claim 9, further comprising:
   (4) using the common focusing element to step through a number of immediately adjacent focal planes of the in-vivo eye;
   (5) averaging the light at the first detector for an interval at each focal plane;
   (6) setting the focus to the focal plane with the maximum fluorescence emission; and
   (7) repositioning the first confocal assembly relative to the first confocal imaging system using an automated algorithm under computer control to maximize throughput at the first detector.

11. The method of claim 10, further comprising:
   (8) adjusting the second confocal imaging system such that the second wavelength light is focused on a desired focal plane of the in-vivo eye; and
   (9) repositioning the second confocal assembly relative to the second confocal imaging system using an automated algorithm under computer control to maximize the second wavelength light throughput at the second detector.

12. The method of claim 1, further comprising repeating steps (b) and (c).

13. The method of claim 1, further comprising repeating steps (k) and (l).

14. The method of claim 8, further comprising repeating steps (1) and (2).

15. The method of claim 10, further comprising repeating steps (4) to (7).

16. The method of claim 11, further comprising repeating steps (8) and (9).

17. The method of claim 11, wherein the first and the second wavelengths are in a range between 0.45 to 1.2 micrometers.

18. The method of claim 11, wherein one of the first and the second wavelengths is in a visible spectrum and suitable for stimulating a fluorescence emission from the in-vivo eye, further wherein one of the second and the first wavelengths is in an infrared spectrum.

19. The method of claim 11, wherein the common focusing element is a deformable mirror.

20. The method of claim 1, wherein the first translation stage is a three-axis translation stage such that the first confocal aperture and the first detector are moved together in three dimensions by the first translation stage.

21. The method of claim 1, wherein the second translation stage is a three-axis translation stage such that the second confocal aperture and the second detector are moved together in three dimensions by the second translation stage.

* * * * *